United States Patent
Zou et al.

(10) Patent No.: US 6,771,074 B2
(45) Date of Patent: Aug. 3, 2004

(54) PROBE ASSEMBLY FOR A FLUID CONDITION MONITOR AND METHOD OF MAKING SAME

(75) Inventors: Lian Q. Zou, Glendale, WI (US); James E. Hansen, Franklin, WI (US); Victor E. Shtaida, Franklin, WI (US)

(73) Assignee: Eaton Corporation, Cleveland, OH (US)

( * ) Notice: Subject to any disclaimer, the term of this patent is extended or adjusted under 35 U.S.C. 154(b) by 0 days.

(21) Appl. No.: 10/060,107

(22) Filed: Jan. 31, 2002

(65) Prior Publication Data

US 2003/0141882 A1 Jul. 31, 2003

(51) Int. Cl.$^7$ .................... G01N 27/02; G01R 27/08
(52) U.S. Cl. ...................... 324/446; 324/698
(58) Field of Search ............... 324/698, 663, 324/686, 687, 688, 696, 722, 446; 73/53.05

(56) References Cited

U.S. PATENT DOCUMENTS

| | | | |
|---|---|---|---|
| 3,559,048 A | 1/1971 | Bryant | 324/30 |
| 5,089,780 A | * 2/1992 | Megerle | 324/448 |
| 6,250,152 B1 | 6/2001 | Klein et al. | 73/304 |
| 6,278,281 B1 | 8/2001 | Bauer et al. | 324/441 |
| 6,380,746 B1 | 4/2002 | Polczynski et al. | 324/446 |

FOREIGN PATENT DOCUMENTS

| | | |
|---|---|---|
| EP | 0543215 | 5/1993 |
| WO | WO 00/34794 | 6/2000 |

OTHER PUBLICATIONS

Smiechowski: "On–Line Electrochemical Sensors for Monitoring Time–Dependent Water–Polymerinteractions in Industrial Lubricants" Electrochemical Society Proceeedings, vol. 2001–18, 2001, pp. 442–453, p. 444.

Fitchner W et al: On–Line Messung Der Eigenschaften Von Schmieroelen Fuer Verbrennungsmotoren Mit Einem Elektrischen Sensor Technisches Messen TM, R. Oldenbourg Verlag, Munchen, DE., vol. 65, No. 2, Feb. 1, 1998 (Jan. 20, 1998), pp. 53–57.

* cited by examiner

*Primary Examiner*—Albert Decady
*Assistant Examiner*—James C. Kerveros
(74) *Attorney, Agent, or Firm*—Roger A. Johnston

(57) ABSTRACT

A probe assembly for use in monitoring fluid conditions in real time in a transducer utilizing impedance spectroscopy and having two closely spaced tubular concentric electrodes. The electrodes have a surface area of about 8.1 to 10.8 cm$^2$ spaced in the range of about 0.1 to 0.55 mm. In one embodiment a concentric outer tubular Faraday shield is employed for monitoring fluid in a non-metallic vessel. The probe assembly is particularly suitable for monitoring hydraulic fluid including automatic transmission fluid and mineral based engine oil for diesel and gasoline engines.

17 Claims, 4 Drawing Sheets

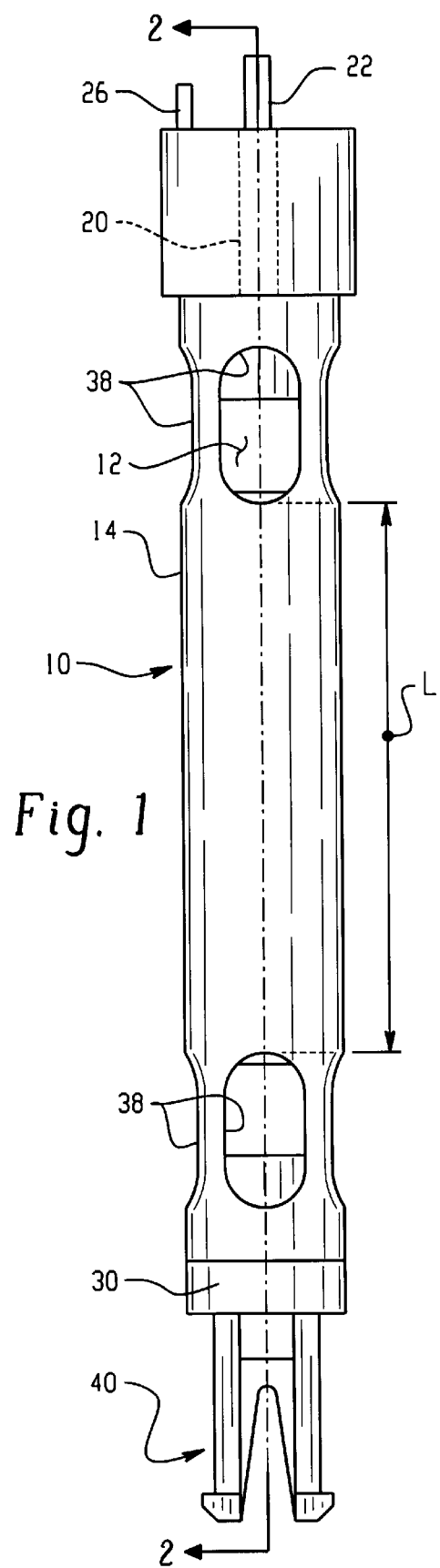
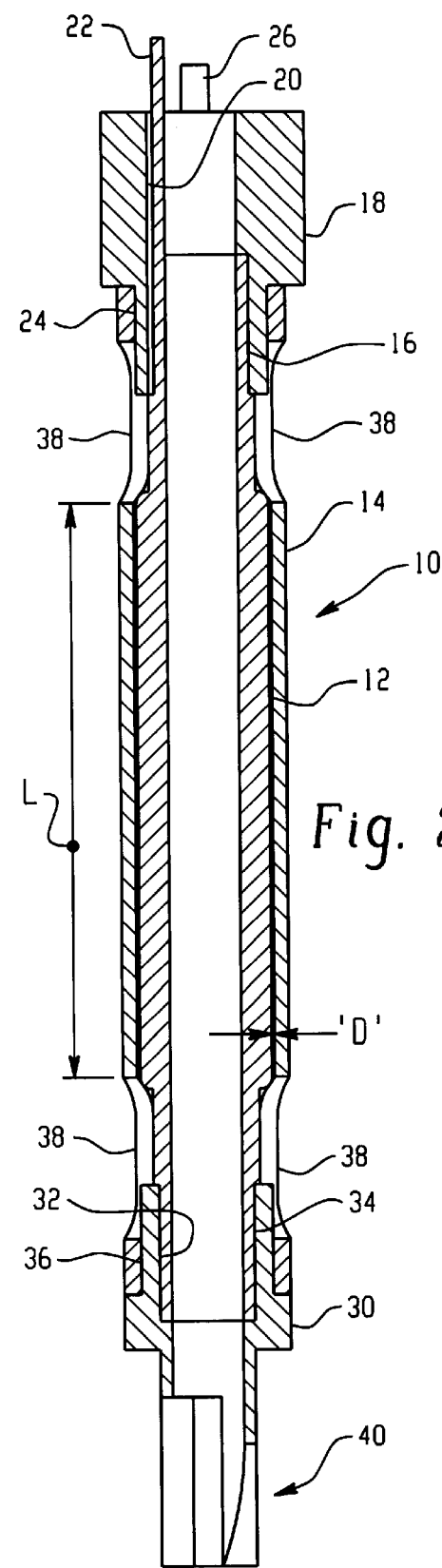
Fig. 1
Fig. 2

PROBE ASSEMBLY FOR A FLUID CONDITION MONITOR AND METHOD OF MAKING SAME

BACKGROUND OF THE INVENTION

The present invention relates to transducers for providing an electrical signal indication in real time of the instantaneous condition of a fluid in an operating system. In particular, the invention relates to fluid condition monitoring in fluids employed for engine lubrication and for hydraulic actuation in power transmission devices such as automatic transmissions for motor vehicles.

It is known to utilize impedance spectroscopy or impedance measurements at different frequencies associated with the bulk fluid impedance and the surface impedance of the electrodes for determining the changed condition of an operating fluid over time and service as described in U.S. Pat. No. 6,278,281 in the name of R. A. Bauer, et al and assigned to the assignee of the present invention. The aforesaid fluid condition monitor utilizes a pair of electrodes disposed in a generally planar array with interdigitated elements thereof or spaced parallel plates and disposed for immersion in the fluid to be monitored. The disadvantage of the probe arrangement of the aforesaid '281 patent to Bauer, et al is that of the difficulty of supporting and shielding such an arrangement from mechanical interference such as that due to vibration or fluid movement such as splashing or pressure perturbations where the probe is intended to be immersed in motor vehicle transmission fluid or engine lubricant at elevated temperatures.

Furthermore the arrangement of the electrode elements in the aforesaid probe and particularly where the electrodes are formed of thin material deposited upon a substrate has proven to be difficult to arrange to provide a required surface area and spacing, not sufficiently robust and relatively high cost in manufacture.

Furthermore, problems have been encountered in providing a sufficiently high signal to noise ratio for probes of the aforesaid type in impedance measurement type fluid monitoring. Therefore, it has been desired to provide an improved probe for a transducer employing the aforesaid impedance spectroscopy techniques for monitoring the condition of a fluid in real time with respect to fluid contamination and constituency changes and to provide such an improved probe that is reliable in harsh service environments and easy to manufacture and relatively low cost at the high volumes required for automotive applications.

BRIEF SUMMARY OF THE INVENTION

The present invention provides a probe assembly intended for use in a transducer utilizing impedance spectroscopy by measuring impedance at different frequencies associated with bulk fluid impedance and surface electrode impedance for monitoring in real time the condition of a fluid such as hydraulic fluid, including automatic transmission fluid and mineral based engine lubricating oil and employs a pair of concentric tubular electrodes for immersion in the fluid to be monitored.

The electrodes of the invention probe assembly may be electrically connected from a correspondingly disposed end thereof attached to a header. If desired, each tubular electrode may have an integral connector terminal formed extending axially therefrom.

The inner tubular electrode has a minimum surface area disposed at a predetermined distance from the inner periphery of the outer tubular electrode. Where the electrode assembly is immersed in fluid contained in a vessel capable of acting as a Faraday shield, in one embodiment, the probe assembly does not require a shield of its own; whereas, if the electrodes are immersed in fluid in a vessel or casing which does not act as a Faraday shield, in another embodiment, the probe employs its own outer tubular Faraday shield. The present invention provides a probe assembly having a pair of concentrically spaced tubular electrodes suitably configured for impedance spectroscopy measurement of fluid condition in real time where the electrode material provides a robust configuration and has a minimum bulk and is easily configured for installation through an aperture formed in the wall of the fluid containing vessel, such as an engine crankcase or transmission casing. Furthermore the present invention provides electrodes arranged for improved signal to noise ratios thereby minimizing the amount of signal conditioning required for remote signal processing. Faraday shield housing can reduce fluid turbulence, maintain better isothermo condition in addition to providing zero E field enclosure to prevent sensing current leakage, and further eliminating EMI.

BRIEF DESCRIPTION OF THE DRAWINGS

FIG. 1 is a side elevation view of one embodiment of the invention suitable for monitoring fluid in a vessel acting as a Faraday shield;

FIG. 2 is a section view taken along section-indicating lines 2—2 of FIG. 1;

DETAILED DESCRIPTION OF THE INVENTION

Figure 3:
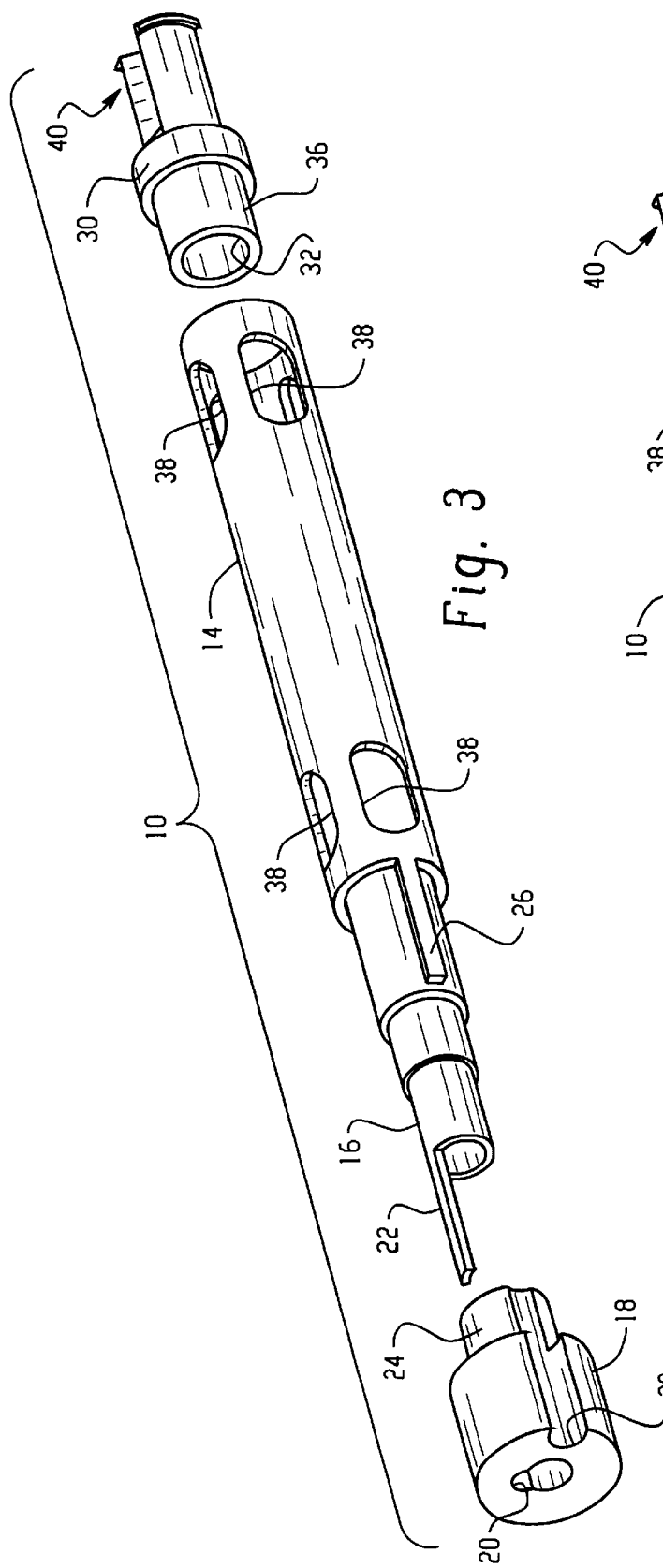
FIG. 3 is an exploded view of the probe assembly of FIG. 1.
Figure 4:
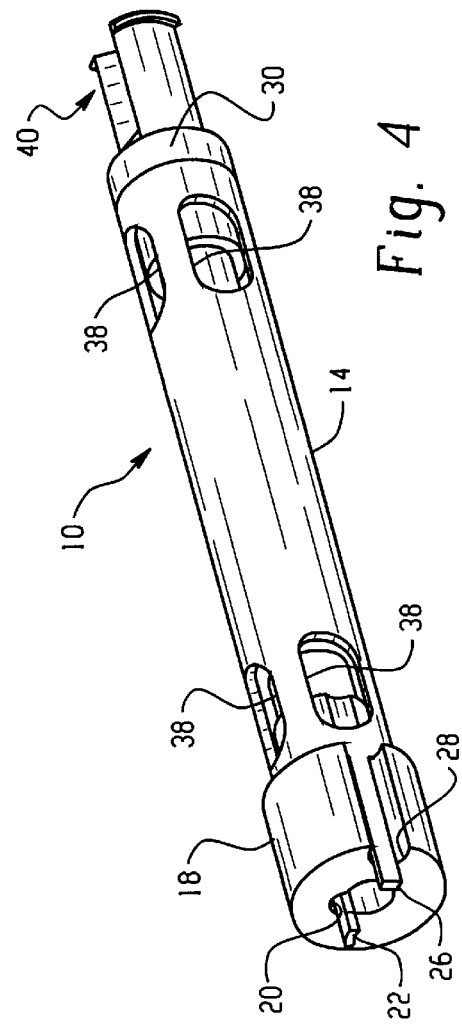
FIG. 4 is a perspective view of the probe assembly of FIG. 1 in the assembled condition.

Referring to FIGS. 1 and 2, an embodiment of the invention suitable for use in monitoring fluid in a motor vehicle automatic transmission is indicated generally at 10 and includes an inner tubular electrode 12 having the outer surface thereof for a length denoted by the reference character L spaced from the inner periphery of an outer tubular electrode 14 by a predetermined amount to thereby provide a specified surface area of electrodes spaced at a known distance.

The inner electrode 12 has a reduced diameter portion 16 which is received in an end header or collar 18 which has a passage 20 therethrough through which is extended a connector terminal 22 preferably formed axially extending and integrally as one piece with the end of the inner electrode 12.

The outer electrode 14 is received over a reduced diameter portion 24 formed on the header 18 for retaining the inner electrode 12 and the outer electrode 14 in the desired spaced relationship. A second electrical terminal 26 extends axially from the end of the outer electrode 14 and is preferably formed integrally therewith as one piece. The terminal 26 passes through a groove 28 (see FIGS. 5 and 6).

Referring to FIGS. 1 through 4, the end of the inner and outer electrodes 12, 14 remote or distal from the header 18 have a distal end header 30 disposed thereon. Header 30 has a counterbore 32 formed therein which is received over a reduced diameter 34 formed on the inner electrode 52; and, header 30 has a reduced outer diameter 36 which is received in close registration with the inner periphery of the outer electrode 14. The outer electrode 14 has a plurality of voids 38 formed therein to permit fluid communication with the space between the inner and outer electrodes.

If desired, the embodiment 10 may have a bifurcated end portion indicated generally at 40 formed on the end of the sleeve 30 and adapted for snap locking attachment thereto for support of the distal end of the probe by external structure (not shown).

In the presently preferred practice, the area of the spaced electrodes spaced by a distance denoted by reference character D is in the range of about 8.1 to 10.8 cm$^2$; and, the spacing is in the range of about 0.15 to 0.55 mm. In the presently preferred practice for monitoring automatic transmission fluid, the gap D for embodiment 10 is preferably nominally about 0.13 mm and the area of the electrode over the length L is 8.1 cm$^2$. Preferably at least one of the electrodes 12, 14 has a wall thickness in the length L of about 1.5 to 2.0 mm.

In the presently preferred practice of the invention, for monitoring based automatic transmission fluid, the spaced D, D' is in the range 0.10 to 0.15 mm. for monitoring mineral based engine lubricant such as used in diesel and gasoline engines, the spacing D, D' is preferably in the range 0.38 to 0.55 mm.

It will be understood that the probe assembly 10 may be installed through a hole in the fluid vessel wall (not shown) having a clearance diameter closely interfitting the outer diameter of the electrode 14 such that the undersurface of header 18 registers against the outer surface of the vessel wall. The distal end of the probe assembly may then, if desired, be supported by connection of the bifurcated end 40 to any suitable supporting structure (not shown) within the fluid vessel. It will be further understood that the probe assembly 10 is intended for installation through the wall of a fluid vessel having sufficient conductive material in the wall thereof to act as a Faraday shield for the tubular electrodes of probe 10 such as, for example, the metallic casing of an automatic transmission or an oil sump housing or crankcase of an engine.

Figure 5:
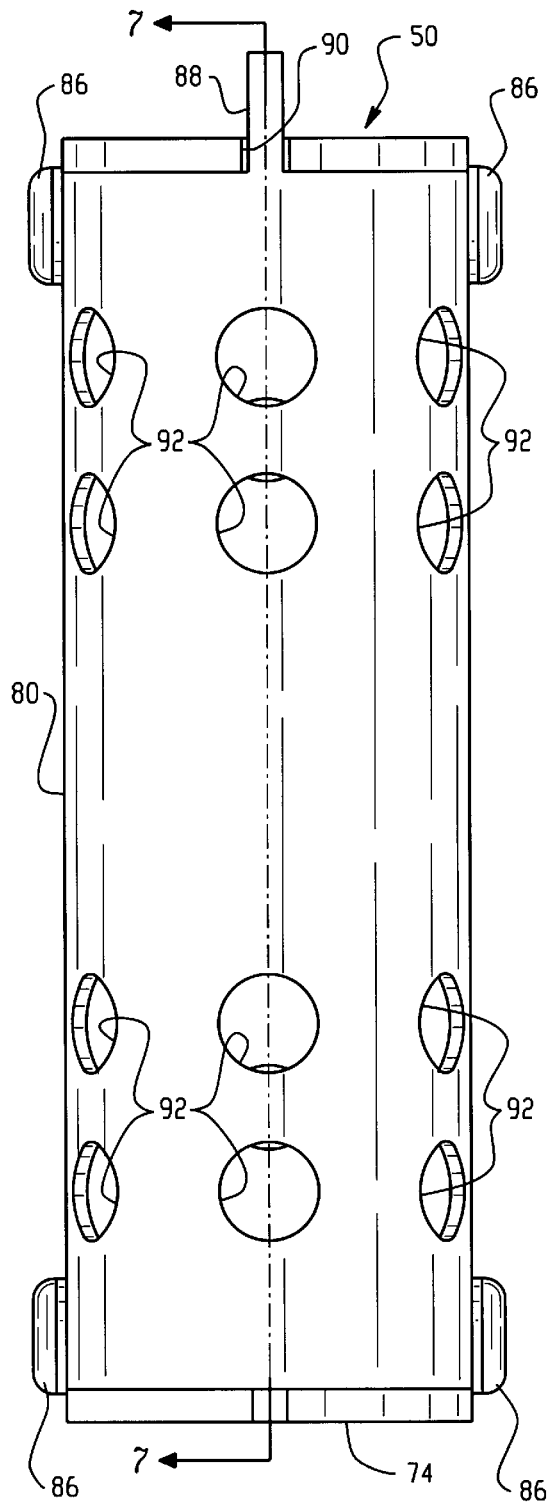
FIG. 5 is a side elevation view of another embodiment of the invention employing a self-contained Faraday shield.
Figure 6:
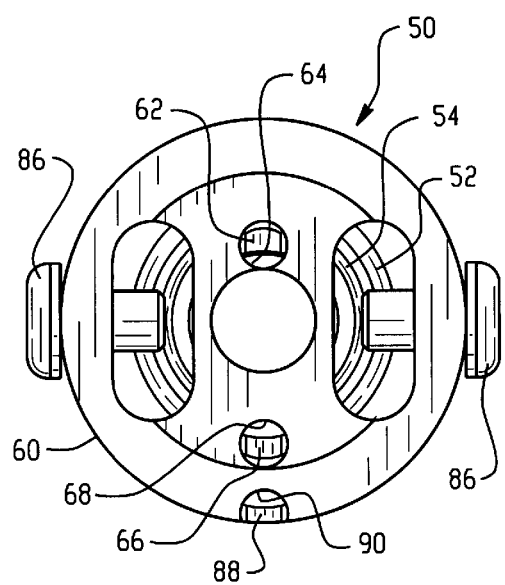
FIG. 6 is a top view of the probe assembly of FIG. 5.
Figure 7:
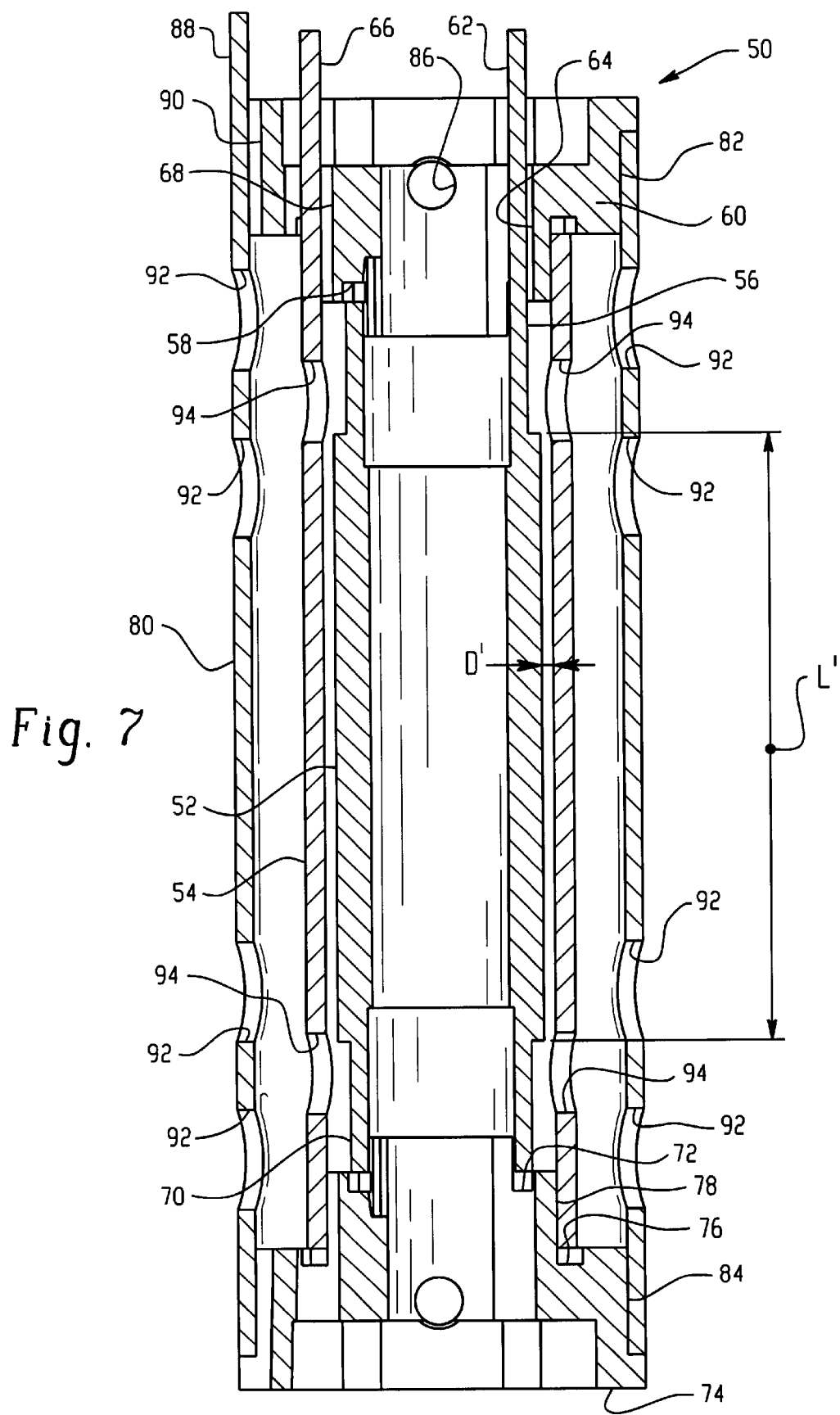
FIG. 7 is a section view taken along section-indicating lines 7—7 of FIG. 5.

Referring to FIGS. 5 through 7, another embodiment of the invention is illustrated generally at 50 and includes an inner tubular electrode 52 having a length L' thereof defining a surface area within the aforesaid range set forth for the embodiment 10 disposed within and at a spacing denoted by the reference character D' from an outer tubular electrode 54 disposed concentrically about the inner electrode 52. It will be understood that the spacing distance D' for the embodiment 50 is within the aforesaid range specified hereinabove for the spacing D of the embodiment 10.

The inner electrode 52 has a reduced diameter portion 56 formed on the upper end thereof which is registered in an annular groove 58 formed in the undersurface of a header 60.

The inner electrode 52 has an electrical connecting terminal 62 preferably formed integrally therewith extending axially through a passage 64 provided in collar 60 and outwardly thereof is shown in FIG. 7.

Outer electrode 54 similarly has an electrical connector terminal 66, preferably formed integrally therewith, and extending axially through a passage 68 formed in the header 60 and axially outwardly thereof.

The distal or lower end of the inner electrode 52 has a reduced diameter portion 70 formed thereon which is received in a groove 72 formed in a lower end header 74. Header 74 has a similar groove 76 formed therein at a larger diameter than groove 72 into which groove 76 is received the lower end of the outer electrode 54. The header 74 has a reduced diameter portion 78 which is slidably received in the inner periphery of the outer electrode 54 in closely fitting arrangement.

An outer tubular Faraday shield 80 is received over the headers 60, 74 and is closely fitted over a reduced diameter portion 82 on header 60 at the upper end of the shield 80. The lower end of shield 80 is received over a reduced diameter 84 formed on the lower header 74 in closely fitting arrangement. The shield is secured to the upper header 60 and lower header 74 by any suitable expedient as, for example, fasteners 86, although it will be understood that other techniques may be employed such as, for example, press fitting, weldment or adhesives. The Faraday shield 80 has an electrical connector terminal 88 formed preferably integrally therewith and extending axially therefrom through a recess or groove 90 formed in the upper header 60.

The probe assembly 50 thus provides a self-contained Faraday shield for the inner and outer electrodes and may be mounted in a fluid vessel which does not provide sufficient shielding of the electrodes.

The Faraday shield 80 has a plurality of apertures 92 formed therein to permit fluid in the vessel to flow to the electrodes encased within the shield 80. Similarly, outer electrode 54 has a plurality of apertures 94 formed therein to permit fluid access to the surfaces of the inner and outer electrodes.

The present invention thus provides an improved probe assembly for use in monitoring condition of a fluid such as hydraulic fluid including automatic transmission fluid or engine lubricant in real time by impedance spectroscopy techniques and provides for improved signal to noise ratio and robustness in construction and relatively low manufacturing cost.

Although the invention has hereinabove been described with respect to the illustrated embodiments, it will be understood that the invention is capable of modification and variation and is limited only by the following claims.

What is claimed is:

1. A method of fluid monitoring by impedance spectroscopy comprising:
    (a) measuring impedance at different frequencies associated with bulk fluid impedance and electrode surface impedance;
    (b) disposing an inner tubular electrode concentrically within an outer tubular electrode and spacing the inner electrode in the range of about 0.15 to 0.55 mm radially from the outer electrode and disposing a surface area of such inner electrode in the range of about 8.1 to 10.8 cm$^2$ at said spacing; and,
    (c) forming an electrical connector terminal at a corresponding end of said inner and outer electrode.

2. The method defined in claim 1, wherein said step of disposing an inner tubular electrode includes attaching a corresponding end of the inner and outer electrode to a common header.

3. The method defined in claim 1, wherein said step of attaching includes passing said connector terminal through the common header.

4. The method defined in claim 1, wherein said step of spacing the inner electrodes includes spacing the inner electrode about 0.15 mm from the outer electrodes for sensing the condition of motor vehicle automatic transmission fluid.

5. The method defined in claim 1, wherein said step of spacing the inner electrode about 0.55 mm from the outer electrode for sensing the condition of diesel engine lubricant.

6. The method defined in claim 1, wherein said step of disposing an inner tubular electrode includes spacing the inner electrode about 0.38 to 0.55 mm from the outer electrode for sensing the condition of mineral oil based engine lubricant.

7. The method defined in claim 1, wherein said step of disposing an inner electrode includes disposing an inner electrode within an outer electrode having a diameter in the range of about 9.5–13 millimeters.

8. The method defined in claim 1, further comprising disposing a tubular shield over said outer electrode.

9. The method defined in claim 1, wherein said step of disposing a shield includes attaching a header to an end of said electrodes and supporting said shield on the header.

10. The method defined in claim 1, wherein said step of disposing an inner electrode includes radially spacing said inner electrode about 0.38 mm from the inner surface of the outer electrode and sensing the condition of diesel engine lubricant.

11. The method defined in claim 1, wherein said step of disposing an inner electrode includes attaching said electrode to a common header.

12. The method defined in claim 1, wherein said step of disposing an inner electrode includes radially spacing said inner electrode about 0.38 mm from the inner surface of the outer electrode and sensing the condition of mineral oil based engine lubricant.

13. A system for fluid condition monitoring in real time comprising: a probe assembly comprising:
(a) an outer electrode having a relatively thin wall tubular configuration, and
(b) an inner electrode having a relatively thin wall tubular configuration and disposed concentrically within said outer electrode, said inner electrode having a radial spacing in the range of about 0.15 to 0.55 mm inwardly from the inner surface of said outer electrode, and said inner electrode further including a surface area in the range of about 8.1 to 10.8 $cm^2$ disposed at said spacing; and, wherein the probe assembly is used to make measurements at different frequencies associated with bulk fluid impedance and surface electrode impedance.

14. A method of fluid monitoring by impedance spectroscopy comprising:
(a) measuring impedance at different frequencies;
(b) disposing an inner tubular electrode concentrically within an outer tubular electrode and spacing the inner electrode in the range of about 0.15 to 0.55 mm radially from the outer electrode and disposing a surface area of such inner electrode in the range of about 8.1 to 10.8 $cm^2$ at said spacing; and,
(c) forming an electrical connector terminal at a corresponding end of said inner and outer electrode.

15. The method defined in claim 14, wherein said step of disposing an inner electrode includes spacing the inner electrode about 0.38 to 0.55 mm from the outer electrode for sensing the condition of diesel engine lubricant.

16. A system for fluid condition monitoring in real time comprising: a probe assembly with:
(a) an outer electrode having a relatively thin wall tubular configuration, and
(b) an inner electrode having a relatively thin wall tubular configuration and disposed concentrically within said outer electrode, said inner electrode having a radial spacing in the range of about 0.15 to 0.55 mm inwardly from the inner surface of said outer electrode, and said inner electrode further including a surface area in the range of about 8.1 to 10.8 $cm^2$ disposed at said spacing; and, wherein the probe assembly is used to make measurements at different frequencies.

17. The system defined in claim 16, wherein said inner electrode is spaced about 0.38 to 0.55 mm from the outer electrode for sensing the condition of diesel engine lubricant.

* * * * *